(12) United States Patent
Thames et al.

(10) Patent No.: US 8,450,414 B2
(45) Date of Patent: May 28, 2013

(54) GLYCEROL ESTER-FREE FUNCTIONALIZED VEGETABLE OIL DERIVATIVES AND THEIR LATEX COMPOUNDS

(75) Inventors: Shelby F. Thames, Hattiesburg, MS (US); James W. Rawlins, Petal, MS (US); Sharathkumar K. Mendon, Hattiesburg, MS (US); David Delatte, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 330 days.

(21) Appl. No.: 12/331,115

(22) Filed: Dec. 9, 2008

(65) Prior Publication Data

US 2009/0143527 A1  Jun. 4, 2009

Related U.S. Application Data

(62) Division of application No. 11/699,693, filed on Jan. 30, 2007, now abandoned.

(51) Int. Cl.
*C08F 2/22* (2006.01)

(52) U.S. Cl.
USPC ......... 524/812; 524/801; 524/804; 526/238.3

(58) Field of Classification Search
USPC .................. 524/801, 804, 812; 526/238.3
See application file for complete search history.

(56) References Cited

U.S. PATENT DOCUMENTS

| | | | |
|---|---|---|---|
| 3,498,958 A * | 3/1970 | Ray-Chaudhuri et al. | 428/507 |
| 3,590,016 A | 6/1971 | Hopwood et al. | |
| 4,910,268 A | 3/1990 | Kobayashi | |
| 5,225,480 A * | 7/1993 | Tseng et al. | 524/813 |
| 5,350,631 A * | 9/1994 | Tseng et al. | 428/343 |
| 6,001,913 A | 12/1999 | Thames | |
| 6,174,948 B1 * | 1/2001 | Thames et al. | 524/398 |
| 6,203,720 B1 | 3/2001 | Thames | |
| 6,245,829 B1 * | 6/2001 | Meij et al. | 522/175 |
| 6,624,223 B1 | 9/2003 | Thames | |
| 6,897,257 B2 | 5/2005 | Thames | |
| 2005/0192383 A1 | 9/2005 | Bloom | |
| 2005/0203246 A1 | 9/2005 | Thames | |
| 2006/0020062 A1 | 1/2006 | Bloom | |

FOREIGN PATENT DOCUMENTS

| | | |
|---|---|---|
| CN | 14025254 | 3/2003 |
| EP | 0971004 A1 | 1/2000 |
| JP | 49-082620 A | 8/1974 |
| JP | 03095565 | 4/1991 |
| WO | WO 9833855 A1 | 8/1998 |
| WO | WO 0144380 | 6/2001 |

OTHER PUBLICATIONS

Akpan et al. Pakistan Journal of Nutrition 5 (2) 106-109 (2006).*
"Soybean Composition and Nutrients". http://chinese-school.netfirms.com/soybean-composition.html. No Author, No Date.*
Hawley's Condensed Chemical Dictionary, Aliphatic, Fatty Acid, 2002, John Wiley & Sons, Inc., 14th Edition (3 pages of abstract and title page).
JP 49-082620, K. Onoda et al., English Language Abstract (one page), Published 1974.
Kato et al., Vinyl-tupe resin particle-containing electrostatograpic liquid developer, 1991, Japanese Patent Office, English Abstract JP03095565.
Jansen, et al., "Fast Monomers," Macromolecules, 2003, pp. 3861-3873, vol. 36, No. 11.
Jansen, et al., "Polymer Preprints," Journal of the American Chemical Society, 42(2):769-770 (2001).
International Search Report and Written Opinion, PCT US/US2008/001088 (Oct. 7, 2008).
Nabuurs et al., "Alkyd-acrylic hybrid systems for use as binders in waterborne paints," Progress in Organic Coatings, 27:163-172 (1996).
Wang et al., "Emulsion and Miniemulsion Copolymerization of Acrylic Monomers in the Presence of Alkyd Resin," Journal of Applied Polymer Science, 60:2069-2076 (1996).
Shoaf et al., "Alkyd/Acrylic Hybrid Latexes with Enhanced Oxidative Curing," Polymer Reaction Engineering, 11(3):319-334 (2003).

* cited by examiner

Primary Examiner — Liam Heincer
Assistant Examiner — Michael A Salvitti
(74) Attorney, Agent, or Firm — Lawrence Arthur Schemmel

(57) ABSTRACT

The present invention is directed to a fatty amide (meth)acrylate monomer, methods of making the monomer, and latex polymers comprising the fatty amide (meth)acrylate monomer. The monomers are derived by reacting unsaturated vegetable oils with ethanolamine or substituted ethanolamine. The vegetable oil derivative is then reacted with either (meth)acryloyl chloride or (meth)acrylic acid to form a fatty amide (meth)acrylate monomer or the product of the reaction of hydroxyethyl (meth)acrylate reacted with isophorone diisocyanate to form a urethane fatty amide (meth)acrylate monomer. The increased hydrophilicity of the fatty amide (meth)acrylate monomer facilitates the diffusion through the aqueous phase. The monomer synthesis is designed to be glycerol ester-free to increase long term stability for monomers and polymers.

16 Claims, No Drawings

GLYCEROL ESTER-FREE FUNCTIONALIZED VEGETABLE OIL DERIVATIVES AND THEIR LATEX COMPOUNDS

BACKGROUND OF THE INVENTION

The present application is a divisional of U.S. application Ser. No. 11/699,693, filed Jan. 30, 2007 now abandoned, the entire contents of which are incorporated herein by reference.

The present invention is directed to vegetable oil derivatives. More particularly, the present invention is directed to functionalized vegetable oil derivative macromonomers that can be used in latexes and coatings.

A key problem encountered by coatings manufacturers is the development of coating formulations with low volatile organic compound (VOC) content. For instance, emulsion polymers are currently formulated with coalescing aids or plasticizers in order to form films at and below ambient conditions yet dry to films of sufficient glass transition temperature ($T_g$) to perform adequately at and above room temperature. However, the coalescing aids evaporate upon application and constitute VOCs. In general, the ability of emulsion polymers to form or coalesce into a smooth film is governed by the minimum film temperature (MFT) of the polymer in question. Low MFT polymers are required in order to exhibit coalescence, flow, and surface wetting properties. However, if the polymer remains soft and tacky, the coatings are not usable. Therefore, it is necessary to develop a technology in which coating formulations contain suitable ingredients to provide an initial low MFT, which, upon application, form non-tacky, durable, hard, and water resistant surfaces having a $T_g$ significantly above their MFT.

Various coating compositions which cure under ambient conditions are known in the prior art. A few such examples involve curing by a chemical reaction such as epoxide-carboxylic acid reaction, isocyanate-moisture reaction, polyaziridine-carboxylic acid reaction, and activated methylene-unsaturated acrylic reaction.

Recently, a number of new latex or emulsion compositions derived from semi-drying and/or non-drying oils have been developed for use in coatings, adhesives and inks. Such compositions are disclosed in U.S. Pat. Nos. 6,001,913; 6,174,948; and 6,203,720 each of which is incorporated herein by reference in its entirety. The inherent hydrophobicity of vegetable oil macromonomers (VOMMs) limits their ability to migrate through the aqueous phase during emulsion polymerization and results in less than random copolymerizability. The VOMMs are likely to remain in the monomer droplets unlike the smaller less hydrophobic comonomers that diffuse through the aqueous phase and randomly polymerize within particles. Eventually, the unpolymerized VOMM droplets coalesce and form a separate phase as they are incompatible with the water and latex particles. It would therefore be an advancement to develop VOMMs with more hydrophilicity to facilitate/promote VOMM diffusion through the aqueous phase. Moreover, long-term storage stability of monomers and polymers is decreased when monomers are synthesized with glycerol esters as esters are susceptible to hydrolysis. It would thus be an additional benefit to synthesize the monomers in the absence of glycerol ester groups to increase long term stability for monomers and polymers.

The search for additional compositions that can be used in latexes and coatings is continuing. Accordingly, it would be an advancement in the art to provide glycerol ester-free compositions made from renewable resources that are suitable for use in latexes and coatings.

SUMMARY OF THE INVENTION

The present invention is directed to functionalized vegetable oil derivatives which are useful in latexes and coatings. In one embodiment, an ethylenically unsaturated vegetable oil is reacted with ethanolamine or substituted ethanolamines to form the hydroxy functional fatty amide. The modified vegetable oil is then reacted with (meth)acryloyl chloride, or the corresponding (meth)acrylic acid to form a fatty amide (meth)acrylate monomer. In another embodiment, the modified vegetable oil can be reacted with the product of the reaction of hydroxyethyl (meth)acrylate reacted with isophorone diisocyanate to form a urethane fatty amide (meth)acrylate monomer. The functionalized vegetable oil derivatives can be formulated into latexes and other coating compositions.

The present invention provides vegetable oil derivatives that are more hydrophilic than vegetable oils and are designed specifically for efficient random emulsion copolymerization. Specifically, the present invention provides glycerol ester-free fatty amide (meth)acrylate monomers.

The present invention is directed to a fatty amide (meth)acrylate monomer of the formula:

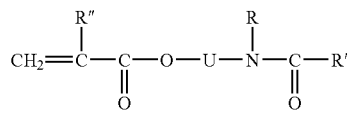

wherein R=$CH_3$, H or $CH_2CH_2OH$
R' =saturated or unsaturated straight chain alkyl group of a fatty acid of vegetable oil;
R" =$CH_3$ or H; and
U=$CH_2CH_2$ or

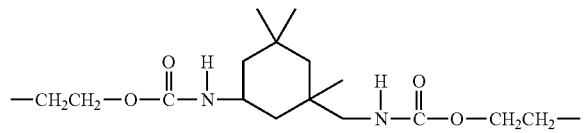

The fatty acid is derived from vegetable oils such as linseed oil, soybean oil, coconut oil, safflower oil, and tung oil. Preferably, the fatty acid is oleic, linoleic, linolenic, caprylic, capric, lauric, palmitic, stearic or eleostearic acid. The present invention is also directed to a latex polymer comprising the polymerization product of an ethylenically unsaturated monomer suitable for forming a latex composition and the modified fatty amide monomer. The present invention also provides a method of making a modified fatty amide monomer comprising the reaction product of a vegetable oil and ethanolamine or substituted ethanolamine; and a (meth)acrylate selected from the group comprising: (meth)acryloyl chloride, (meth)acrylic acid, and the product of hydroxyethyl (meth)acrylate reacted in equimolar proportion with isophorone diisocyanate.

DETAILED DESCRIPTION OF THE PREFERRED EMBODIMENTS

The present invention is directed to a series of vegetable oil macromonomers and their use in latexes and coatings. The invention is also directed to the method of producing these macromonomers. The monomers are derived by reacting unsaturated vegetable oils with ethanolamine or substituted ethanolamine. The vegetable oil derivative is then reacted with either (meth)acryloyl chloride or (meth)acrylic acid to form a fatty amide (meth)acrylate monomer or the product of the reaction of hydroxyethyl (meth)acrylate reacted with isophorone diisocyanate to form a urethane fatty amide (meth)acrylate monomer.

In a preferred embodiment, a vegetable oil such as soybean oil, coconut oil, or linseed oil is reacted with ethanolamine (or substituted ethanolamine) followed by reaction with (meth)acryloyl chloride or (meth)acrylic acid to form the fatty amide (meth)acrylate monomer. Examples of substituted ethanolamines include N-methyl ethanolamine, N-oleoylethanolamine, N-ethylethanolamime, N-propylethanolamine, N-butylethanolamime, N-tert-butylethanolamine, N-(tert-butoxycarbonyl)ethanolamine, N-(allyloxycarbonyl)ethanolamine, benzyl N-(2-hydroxyethyl)carbamate, ethyl-N-(2-hydroxyethyl)-carbamate, and diethanolamine. The reaction mechanism is schematically shown in Reaction 1.

REACTION 1:

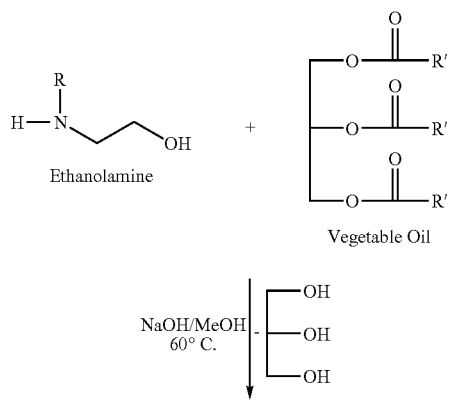

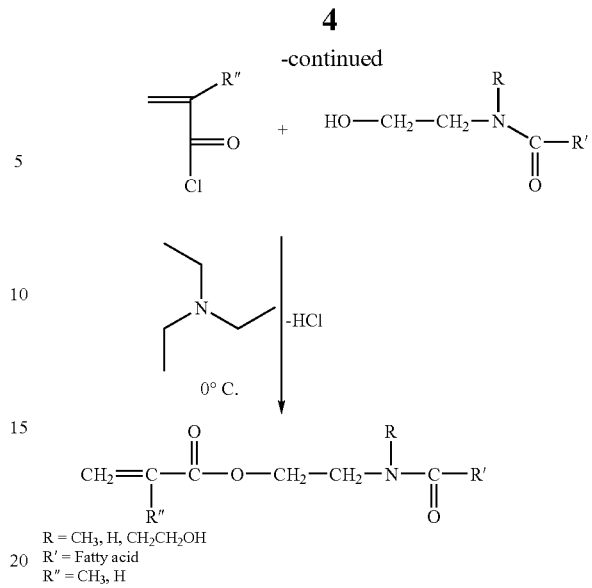

Any vegetable oil can be used in the present invention. However, linseed oil, soybean oil and coconut oil are preferred.

Various compounds can be used to modify the fatty amide. Examples include but are not limited to (meth)acryloyl chloride and (meth)acrylic acid.

In another preferred embodiment, urethane fatty amide monomers are synthesized. First, hydroxyethyl (meth)acrylate is reacted with isophorone diisocyanate. In a preferred embodiment, the hydroxyl (meth)acrylate is reacted in equimolar proportion with isophorone diisocyanate. In a separate reaction, a vegetable oil, for example, soybean oil, coconut oil, or linseed oil is reacted with ethanolamine (or substituted ethanolamine) to form the hydroxyl functional fatty amide. The products of the two reactions were reacted to form the urethane fatty amide (meth)acrylate monomer schematically shown in Reaction 2.

REACTION 2:

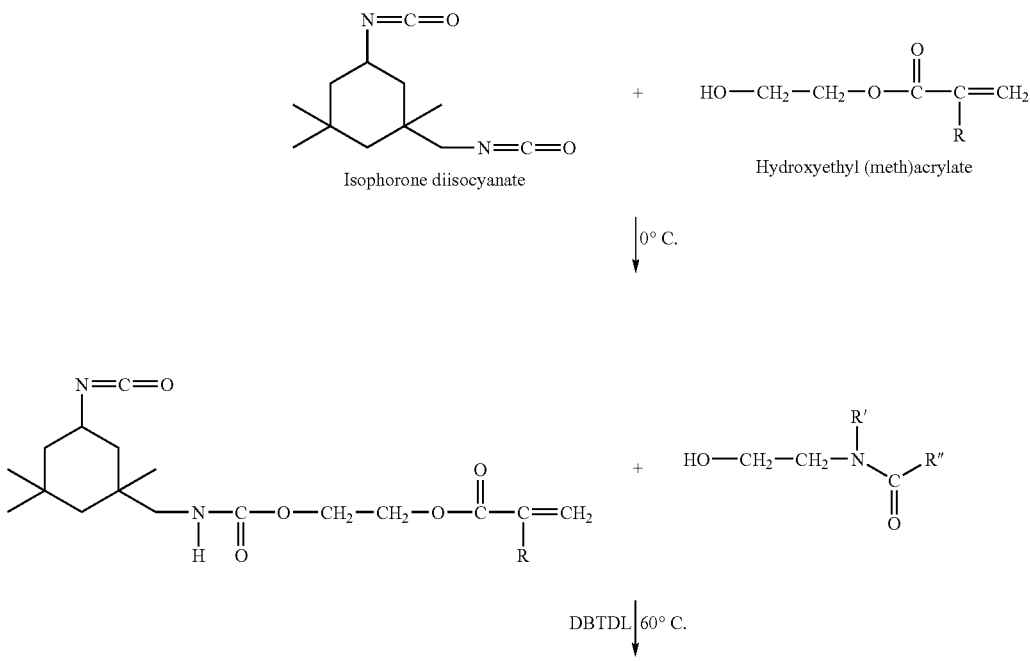

-continued

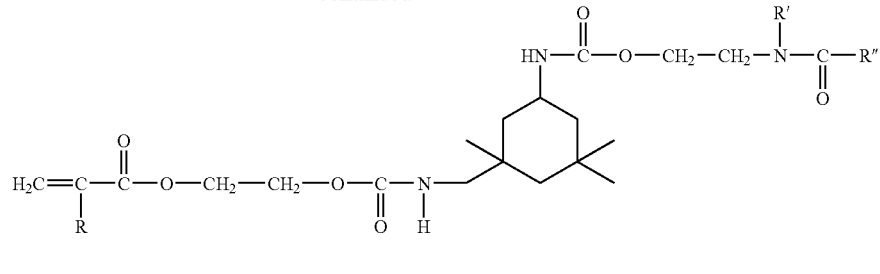

R = CH₃, H
R' = CH₃, H, CH₂CH₂OH
R" = Fatty acid

The macromonomers of the present invention can be used to make latexes and coatings compositions. The monomers described in this patent application can be polymerized in a single or multi-stage emulsion polymerization process to include macroemulsion, miniemulsion, microemulsion and processing can be batch, semi-batch or continuous. Although it is possible to use this monomer in a staged emulsion polymerization, as disclosed in published U.S. Application 2003/0045609, the teachings of which are hereby incorporated by reference, it is not a requirement for efficient polymerization. A latex polymer can be formed from the polymerization product of the fatty amide (meth)acrylate monomer and an ethylenically unsaturated monomer suitable for forming a latex composition. Suitable ethylenically unsaturated monomers include vinyl acetate, vinyl chloride, vinyl ester of a saturated tertiary branched carboxylic acid, acrylonitrile, acrylamide, 2-ethylhexyl acrylate, 2-ethylhexyl methacrylate, 2-hydroxyethyl acrylate, 2-hydroxyethyl methacrylate, glycidyl acrylate, glycidyl methacrylate, acrylic acid, methacrylic acid, butyl acrylate, butyl methacrylate, methyl methacrylate, methyl acrylate, p-acetoxystyrene, and styrene.

The invention is further understood by reference to the following examples which describe the formation of various macromonomers as well as the formulation of latexes and coatings.

EXAMPLES

Example 1

SoyA-1

A three-neck, 1000 mL round bottom flask was purged with nitrogen once equipped with mechanical stirrer, thermometer, condenser and was charged with 500 g soybean oil. Nitrogen was bubbled through the oil overnight to deoxygenate the oil. The flask was placed in an oil bath at 80° C., and 50 g of a sodium methoxide methanol solution (25% in methanol) was added to the flask. The reaction mixture was equilibrated to 80° C., and 125.46 g of N-methyl ethanolamine was added to the flask. An exotherm of approximately 10° C. was noted. The reaction was maintained and the reaction progress was monitored by Fourier transform infrared spectroscopy (FTIR). Complete conversion via FTIR was observed after 4 hours. The reactor was cooled to ambient conditions and diluted with 100 g of methylene chloride. The contents were washed three times with 500 mL of brine (5% sodium chloride). The aqueous phase was discarded and the organic phase was dried with magnesium sulfate. Methylene chloride was removed under reduced pressure, and the product (SoyA-1) was characterized by gel permeation chromatography (GPC), high pressure liquid chromatography (HPLC), and nuclear magnetic resonance (NMR) spectroscopy.

Example 2

SoyA-2

A three-neck, 1000 mL round bottom flask was purged with nitrogen once equipped with mechanical stirrer, thermometer, condenser and was charged with 500 g soybean oil. Nitrogen was bubbled into the mixture overnight to deoxygenate the oil. The flask was placed in an oil bath at 80° C., and 50 g of a sodium methoxide methanol solution (25% in methanol) was added to the flask. The reaction mixture was equilibrated to 80° C., and 186.05 g of ethanolamine was added to the flask. An exotherm of approximately 10° C. was noted. The reaction was maintained and the reaction progress was monitored by Fourier transform infrared spectroscopy (FTIR). Complete conversion via FTIR was observed after 4 hours. The reactor was cooled to ambient conditions and diluted with 100 g of methylene chloride. The contents were washed three times with 500 mL of brine (5% sodium chloride). The aqueous phase was discarded and the organic phase was dried with magnesium sulfate. Methylene chloride was removed under reduced pressure, and the product (SoyA-2) was characterized by GPC, HPLC, and NMR spectroscopy.

Example 3

SoyAA-1

A three-neck, 1000 mL round bottom flask equipped with thermometer, mechanical stirrer, and addition funnel was charged with 250.00 g of SoyA-1, 100.00 mL of methylene chloride, and 74.94 g of triethylamine. The flask was placed in an ice bath and equilibrated to 0° C. 70.00 g of acryloyl chloride was charged to the addition funnel, and added dropwise into the flask over 4 hours. The flask was allowed to equilibrate to ambient conditions overnight. The contents were washed 5 times with 500 mL of brine (5% sodium chloride) to remove unreacted acryloyl chloride, triethylamine, and hydrochloric acid. The aqueous phase was discarded and the organic phase was dried with magnesium sulfate. Methylene chloride was removed under reduced pressure, and the product (SoyAA-1) was characterized by GPC, HPLC, and NMR spectroscopy.

Example 4

SoyAA-2

A three-neck, 1000 mL round bottom flask equipped with thermometer, mechanical stirrer, and addition funnel was charged with 250.00 g of SoyA-2, 100.00 mL of methylene chloride, and 78.19 g triethylamine. The flask was placed in an ice bath and equilibrated to 0° C. 70.00 g of acryloyl chloride was charged to the addition funnel, and added dropwise into the flask over 4 hours. The flask was allowed to equilibrate to ambient conditions overnight. The reactor contents were washed 5 times with 500 mL of brine (5% sodium chloride) to remove unreacted acryloyl chloride, triethylamine, and hydrochloric acid. The aqueous phase was discarded and the organic phase was dried with magnesium sulfate. Methylene chloride was removed under reduced pressure, and the product (SoyAA-2) was characterized by GPC, HPLC, and NMR spectroscopy.

Example 5

CocoA-1

A three-neck, 1000 mL round bottom flask was purged with nitrogen after being equipped with a mechanical stirrer, thermometer, condenser and was charged with 500 g coconut oil. Nitrogen was bubbled through the oil overnight to deoxygenate the oil. The flask was placed in an oil bath at 80° C., and 50 g of a sodium methoxide methanol solution (25% in methanol) was added to the flask. The reaction mixture was equilibrated to 80° C., and 125.46 g of N-methyl ethanolamine was added to the flask. An exotherm was noted. The reaction was maintained at 80° C. and the reaction progress was monitored by FTIR. Complete conversion was observed after 4 hours. The reactor was then cooled to ambient conditions and 100 g of methylene chloride was added to the flask. The contents were washed three times with 500 mL of brine (5% sodium chloride). The aqueous phase was discarded and the organic phase was dried with magnesium sulfate. Methylene chloride was removed under reduced pressure, and the product (CocoA-1) was characterized by GPC, HPLC, and NMR spectroscopy.

Example 6

CocoAA-1

A three-neck, 1000 mL round bottom flask equipped with thermometer, mechanical stirrer, and addition funnel was charged with 401.62 g of CocoA-1, 100.00 mL of methylene chloride, and 120.40 g of triethylamine. The flask was placed in an ice bath and equilibrated to 0° C. 107.69 g of acryloyl chloride was charged to the addition funnel, and added dropwise into the flask over 4 hours. The flask was allowed to equilibrate to ambient conditions overnight. The contents were washed 5 times with 500 mL of brine (5% sodium chloride) to remove unreacted acryloyl chloride, triethylamine, and hydrochloric acid. The aqueous phase was discarded and the organic phase was dried with magnesium sulfate. Methylene chloride was removed under reduced pressure, and the product (CocoAA-1) was characterized by GPC, HPLC, and NMR spectroscopy.

Example 7

SoyUA-1

A three-neck, 500 mL round bottom flask equipped with thermometer, mechanical stirrer, and addition funnel was charged with 64.44 g isophorone diisocyanate and 0.02 g dibutyl tin dilaurate. 33.64 g hydroxylethyl acrylate was charged to the addition funnel and added dropwise to the flask over 4 hours. Next, the addition funnel was charged with 100.00 g SoyA-1, and added to the flask over 1 hour. The reaction progress was monitored by FTIR, and deemed complete when residual isocyanate could not be identified in the FTIR spectra. The product (SoyUA-1) was characterized by GPC, HPLC, and NMR spectroscopy.

Example 8

LinA-1

A three-neck, 1000 mL round bottom flask purged with nitrogen was equipped with mechanical stirrer, thermometer, condenser and was charged with 250 g coconut oil. Nitrogen was bubbled through the oil overnight to deoxygenate the oil. The flask was placed in an oil bath at 80° C., and 25 g of a sodium methoxide methanol solution (25% in methanol) was added to the flask. The reaction mixture was equilibrated to 80° C., and 63.78 g of N-methyl ethanolamine was added to the flask. An exotherm was noted. The reaction was maintained at 80° C. and the reaction progress was monitored by FTIR. Complete conversion was observed after 4 hours. The reactor was cooled to ambient conditions and 100 g of methylene chloride was added to the flask. The contents were washed three times with 500 mL of brine (5% sodium chloride). The aqueous phase was discarded and the organic phase was dried with magnesium sulfate. Methylene chloride was removed under reduced pressure, and the product (LinA-1) was characterized by GPC, HPLC, and NMR spectroscopy.

Example 9

LinAA-1

A three-neck, 500 mL round bottom flask equipped with thermometer, mechanical stirrer, and addition funnel was charged with 200.00 g of LinA-1, 100.00 mL of methylene chloride, and 60.00 g of triethylamine. The flask was placed in an ice bath and equilibrated to 0° C. 60.00 g of acryloyl chloride was charged to the addition funnel, and added dropwise into the flask over 2 hours. The flask was allowed to equilibrate to ambient conditions overnight. The contents were washed 5 times with 500 mL of brine (5% sodium chloride) to remove unreacted acryloyl chloride, triethylamine, and hydrochloric acid. The aqueous phase was discarded and the organic phase was dried with magnesium sulfate. Methylene chloride was removed under reduced pressure, and the product (LinAA-1) was characterized by GPC, HPLC, and NMR spectroscopy.

Example 10

SoyMA-1

A three-neck, 1000 mL round bottom flask equipped with thermometer, mechanical stirrer, and addition funnel was charged with 200.00 g of SoyA-1, 100.00 mL of methylene chloride, and 55.06 g of triethylamine. The flask was placed in an ice bath and equilibrated to 0° C. 49.25 g of methacryloyl chloride was charged to the addition funnel, and added dropwise into the flask over 2 hours. The flask was allowed to equilibrate to ambient conditions overnight. The reactor contents were washed 5 times with 500 mL of brine (5% sodium chloride) to remove unreacted acryloyl chloride, triethylamine, and hydrochloric acid. The aqueous phase was discarded and the organic phase was dried with magnesium sulfate. Methylene chloride was removed under reduced pressure, and the product (SoyMA-1) was characterized by GPC, HPLC, and NMR spectroscopy.

Example 11

SoyAA-1 Esterification Via Acrylic Acid

A 500 mL round bottom flask was charged with 100.0 g SoyA-1, 21.5 g acrylic acid, and 100.0 g toluene. The mixture was heated to 100° C. and 2.5 g methane sulfonic acid was added. The reaction was continued until no further water was released. The toluene was removed under reduced pressure to yield SoyAA-1 and characterized by GPC, HPLC, and NMR spectroscopy.

Example 12

LinUA-1

A three-neck, 1000 mL round bottom flask equipped with thermometer, mechanical stirrer, and addition funnel was charged with 111.11 g isophorone diisocyanate, 60.0 g hexane, 0.17 g phenothiazine (PTZ), 0.17 g methyl hydroquinone (MeHQ) and 0.02 g dibutyl tin dilaurate. 58.00 g hydroxylethyl acrylate was charged to the addition fiunnel and added dropwise to the flask over 2 hours. The temperature was raised to 65° C. and 168.78 g of LinA-1 was added to the flask through the addition funnel over 1 hour. The reaction progress was monitored by FTIR, and deemed complete when residual isocyanate could not be identified in the FTIR spectra. The hexane was removed under reduced pressure, and the product (LinUA-1) was characterized by GPC, HPLC, and NMR spectroscopy.

Example 13

Soy-TungA-1

A three-neck, 1000 mL round bottom flask was purged with nitrogen while equipped with mechanical stirrer, thermometer, condenser and was charged with 150.00 g of soybean oil and 150.00 g of tung oil. Nitrogen was bubbled through the oil overnight to deoxygenate the oil. The flask was placed in an oil bath at 80° C., and 24 g of a sodium methoxide methanol solution (25% in methanol) was added to the flask. The reaction mixture was equilibrated to 80° C., and 125.46 g of N-methyl ethanolamine was added to the flask. An exotherm of approximately 10° C. was noted. The reaction was maintained at 80° C. and the progress was monitored by FTIR. Complete conversion was observed after 4 hours. The reactor was then cooled to ambient conditions and 100 g of methylene chloride was added to the flask. The contents were washed three times with 500 mL of brine (5% sodium chloride). The aqueous phase was discarded and the organic phase was dried with magnesium sulfate. Methylene chloride was removed under reduced pressure, and the product (Soy-TungA-1) was characterized by GPC, HPLC, and NMR spectroscopy.

Example 14

Soy-TungAA-1

A three-neck, 500 mL round bottom flask equipped with thermometer, mechanical stirrer, and addition funnel was charged with 250.00 g of Soy-TungA-1, 100.00 mL of methylene chloride, and 74.94 g of triethylamine. The flask was placed in an ice bath and equilibrated to 0° C. 67.03 g of acryloyl chloride was charged to the addition funnel, and added dropwise into the flask over 2 hours. The flask was allowed to equilibrate to ambient conditions overnight. The reactor contents were washed 5 times with 500 mL of brine (5% sodium chloride) to remove unreacted acryloyl chloride, triethylamine, and hydrochloric acid. The aqueous phase was discarded and the organic phase was dried with magnesium sulfate. Methylene chloride was removed under reduced pressure, and the product (SoyTung AA-1) was characterized by GPC, HPLC, and NMR spectroscopy.

Example 15

Control Latex

A 1 L kettle was charged with 130.00 g of deionized (DI) water and 1.21 g of Rhodapex® CO-436, purged with nitrogen for 15 minutes, and stirred while heating to 70° C. The seed was prepared by preemulsifying a mixture of DI water (8.80 g), Rhodapex CO-436 (0.55 g), Igepal® CO-887 (0.20 g), butyl acrylate (8.20 g), methyl methacrylate (6.30 g), and methacrylic acid (0.10 g) at 1,800 rpm for 20 minutes, and was transferred to the kettle. Ammonium persulfate (2.80 g) was dissolved in 30.00 g of DI water and 3.3 mL of this solution was added to the kettle. Meanwhile, a monomer feed was prepared by preemulsifying a mixture of DI water (160.00 g), sodium bicarbonate (1.65 g), Rhodapex CO-436 (6.00 g), Igepal CO-887 (5.00 g), butyl acrylate (150.00 g), methyl methacrylate (170.00 g), and methacrylic acid (6.00 g) at 1,800 rpm for 20 minutes. The monomer feed was added to the kettle over 2 hours while the remaining initiator solution was added over a period of 2.25 hours. After complete addition, the reaction was allowed to continue at 70° C. for 4 hours. Two chaser solutions were prepared—one by dissolving t-butyl hydroperoxide (0.36 g) in 10.00 g of DI water and the other by dissolving sodium bisulfite (0.35 g) in 10.00 g of DI water. Both chaser solutions were fed to the kettle over a period of 1 hour, and the emulsion was allowed to cool to ambient temperature and discharged.

Example 16

SoyAA-1 Latex

A 1 L kettle was charged with 130.00 g of DI water and 1.21 g of Rhodapex CO-436, purged with nitrogen for 15 minutes, and stirred while heating to 70° C. The seed was prepared by preemulsifying a mixture of DI water (8.80 g), Rhodapex CO-436 (0.55 g), Igepal CO-887 (0.20 g), butyl acrylate (8.20 g), methyl methacrylate (6.30 g), and methacrylic acid (0.10 g) at 1,800 rpm for 20 minutes, and was transferred to the kettle. Ammonium persulfate (2.80 g) was dissolved in 30.00 g of DI water and 3.3 mL of this solution was added to the kettle. Meanwhile, a monomer feed was prepared by preemulsifying a mixture of DI water (160.00 g), sodium bicarbonate (1.65 g), Rhodapex CO-436 (6.00 g), Igepal CO-887 (5.00 g), butyl acrylate (85.00 g), methyl methacrylate (170.00 g), SoyAA-1 (65.00 g), and methacrylic acid (6.00 g) at 1,800 rpm for 20 minutes. The monomer feed was added to the kettle over 2 hours while the remaining initiator solution was added over a period of 2.25 hours. After complete addition, the reaction was allowed to continue at 70° C. for 4 hours. Two chaser solutions were prepared—one by dissolving t-butyl hydroperoxide (0.36 g) in 10.00 g of DI water and the other by dissolving sodium bisulfite (0.35 g) in 10.00 g of DI water. Both chaser solutions were fed to the kettle over a period of 1 hour, and the emulsion was allowed to cool to ambient temperature and discharged.

Example 17

Semi-Gloss Coatings

The latexes described in Examples 15 and 16 were formulated into semi-gloss coatings as per the formulation shown in Table 2.

TABLE 2

Semi-gloss Coating

| Ingredient | Weight (g) |
|---|---|
| Grind | |
| Water | 225.00 |
| Natrosol Plus ® 330 | 2.00 |
| Potassium carbonate | 1.00 |
| Tamol ® 731A | 10.00 |
| Triton ® CF-10 | 2.00 |
| Kathon LX ® 1.5% | 1.50 |
| Ti-Pure ® 706 | 240.00 |
| Polygloss ® 90 | 20.00 |
| Attagel ® 50 | 4.00 |
| Letdown | |
| Water | 60.00 |
| Drewplus ® L-475 | 3.00 |
| Drewthix ® 864 | 2.00 |
| Aquaflow NHS ® 300 | 12.00 |
| Latex | 500.00 |

The coatings were evaluated for their performance properties and the results are listed in Table 3.

TABLE 3

Coating Properties

| Property | Control Coating | SoyAA-1 Coating |
|---|---|---|
| ICI viscosity, Poises | 0.51 | 0.55 |
| Stormer viscosity, KU | 109 | 106 |
| Scrub resistance (1 week) | 362 | 569 |
| Adhesion (1 week) | 2B | 3.5B |
| Gloss (60°) | 27.3 | 20.9 |
| Wet adhesion (1 week) | >1200 | >1200 |

Example 18

SoyAA-1 Latex with Diacetone Acrylamide

A 500 mL kettle was charged with 110.00 g of DI water and 0.80 g of Rhodapex CO-436, purged with nitrogen for 15 minutes, and stirred while heating to 70° C. The seed was prepared by preemulsifying a mixture of DI water (6.00 g), Rhodapex CO-436 (0.37 g), Igepal CO-887 (0.13 g), butyl acrylate (5.50 g), methyl methacrylate (4.20 g), and methacrylic acid (0.07 g) at 1,800 rpm for 20 minutes, and was transferred to the kettle. Ammonium persulfate (2.80 g) was dissolved in 30.00 g of DI water and 3.3 mL of this solution was added to the kettle. Meanwhile, the monomer feed was prepared by preemulsifying a mixture of DI water (107.00 g), sodium bicarbonate (1.10 g), Rhodapex CO-436 (4.00 g), Igepal CO-887 (3.33 g), butyl acrylate (74.70 g), methyl methacrylate (82.70 g), styrene (20.00 g), methacrylic acid (4.00 g), diacetone acrylamide (3.08 g), and SoyAA-1 (36.00 g) at 1,800 rpm for 20 minutes. The monomer feed was added to the kettle over 2 hours while the remaining initiator solution was added over a period of 2.25 hours. After complete addition, the reaction was allowed to continue at 70° C. for 4 hours. Two chaser solutions were prepared—one by dissolving t-butyl hydroperoxide (0.36 g) in 10.00 g of DI water and the other by dissolving sodium bisulfite (0.35 g) in 10.00 g of DI water. Both chaser solutions were fed to the kettle over a period of 1 hour. The emulsion was allowed to cool to ambient temperature and the pH was adjusted to 9 by adding ammonia followed by adipic dihydrazide solution (4.6 g in 11.00 g of DI water).

Example 19

LinAA-1 Latex with Diacetone Acrylamide

A 500 mL kettle was charged with 110.00 g of DI water and 0.80 g of Rhodapex CO-436, purged with nitrogen for 15 minutes, and stirred while heating to 70° C. The seed was prepared by preemulsifying a mixture of DI water (6.00 g), Rhodapex CO-436 (0.37 g), Igepal CO-887 (0.13 g), butyl acrylate (5.50 g), methyl methacrylate (4.20 g), and methacrylic acid (0.07 g) at 1,800 rpm for 20 minutes, and was transferred to the kettle. Ammonium persulfate (2.80 g) was dissolved in 30.00 g of DI water and 3.3 mL of this solution was added to the kettle. Meanwhile, the monomer feed was prepared by preemulsifying a mixture of DI water (107.00 g), sodium bicarbonate (1.10 g), Rhodapex CO-436 (4.00 g), Igepal CO-887 (3.33 g), butyl acrylate (74.70 g), methyl methacrylate (82.70 g), styrene (20.00 g), methacrylic acid (4.00 g), diacetone acrylamide (3.08 g), and LinAA-1 (36.00 g) at 1,800 rpm for 20 minutes. The monomer feed was added to the kettle over 2 hours while the remaining initiator solution was added over a period of 2.25 hours. After complete addition, the reaction was allowed to continue at 70° C. for 4 hours. Two chaser solutions were prepared—one by dissolving t-butyl hydroperoxide (0.36 g) in 10.00 g of DI water and the other by dissolving sodium bisulfite (0.35 g) in 10.00 g of DI water. Both chaser solutions were fed to the kettle over a period of 1 hour. The emulsion was allowed to cool to ambient temperature and the pH was adjusted to 9 by adding ammonia followed by adipic dihydrazide solution (4.6 g in 11.00 g of DI water).

REFERENCES

Thames, Shelby F.; Smith, Oliver W.; Evans, James M.; Dutta, Sandipan; Chen, Lianzhou. (University of Southern Mississippi, USA). Functionalized vegetable oil derivatives used in latex and coating compositions and their preparation. U.S. Pat. Appl. Publ. (2005), 10 pp. CODEN: USXXCO US 2005203246 A1 20050915 Patent written in English. Application: US 2004-800410 20040312. Priority. CAN 143:307794 AN2005:1004384 CAPLUS Xu, Yuanhao; Liu, Fuchang; Wan, Zhong; Liu, Wenlin; Hou, Peimin. Aqueous acrylic acid-modified alkyd amino resin baking paints. Faming Zhuanli Shenqing Gongkai Shuomingshu (2003), 11 pp. CODEN: CNXXEV CN 1405254 A 20030326 CAN 142:200150 AN 2004:687257 CAPLUS Thames, Shelby Freland; Wang, Zhiyu; Brister, Elizabeth H.; Hariharan, Rajan; King, Corey L.; Panjnani, Kamlesh Gopichand. Internally plasticized and low-VOC latex compositions and their applications. U.S. (2003), 25 pp., Cont.-in-part of U.S. Ser. No. 773,741. CODEN: USXXAM U.S. Pat. No. 6,624,223 Bi 20030923 CAN 139:262270 AN 2003:749999 CAPLUS Thames, Shelby F.; Smith, Oliver W.; Chen, Sheng; Blackwell, Catherine C. Preparation of latex polymers containing ethylenically unsaturated derivatives of fatty acids and/or oils by two-stage emulsion polymerization. U.S. Pat. Appl. Publ. (2003), 9 pp., Cont.-in-part of U.S. Ser. No. 460,946. CODEN: USXXCO US 2003045609 A1 20030306 CAN 138:205825 AN 2003:174494 CAPLUS Thames, Shelby Freland; Wang, Zhiyu; Hariharan, Rajan; Panjnani, Kamlesh Gopichand; Brister, Elizabeth H.; King, Corey L. Internally plasticized and low VOC latex compositions, ethylenically unsaturated carboxylate monomer, and their coating, adhesive or ink applications. PCT Int. Appl. (2001), 62 pp. CODEN: PIXXD2 WO 2001044380 A2 20010621 CAN 135:47673 AN2001:453182 CAPLUS Bloom, Paul D. Epoxidized esters of vegetable oil fatty acids as reactive diluents. U.S. Pat. Appl. Publ. (2006), 19 pp-CODEN: USXXCO US 2006020062 A1 20060126 CAN 144:130749 AN 2006:79094 CAPLUS Bloom, Paul D.; Tabuena-Salyers, Teodora R. Thickening systems and aqueous coating compositions, and method for their manufacture and use. U.S. Pat. Appl. Publ. (2005), 17 pp. CODEN:USXXCO US 2005192383 A1 20050901 CAN143:249817 AN2005:963821 CAPLUS

What is claimed is:

1. A latex polymer comprising the emulsion polymerization product of:
    an aqueous dispersed ethylenically unsaturated monomer suitable for forming a latex composition; and
    an aqueous dispersed fatty amide (meth)acrylate monomer of the formula:

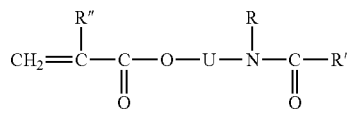

wherein R=CH$_3$, H or CH$_2$CH$_2$OH
    R'=unsaturated or a mixture of unsaturated and saturated straight chain hydrocarbon groups of a fatty acid of a vegetable oil;
    R"=CH$_3$ or H; and
    U =

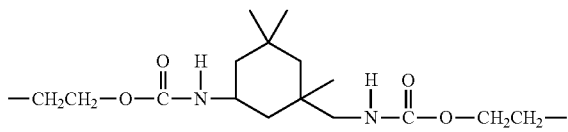

said product being a latex polymer and
    wherein the fatty amide (meth)acrylate monomer is completely polymerized by emulsion polymerization and the fatty amide (meth)acrylate monomer content of the latex composition is 18 weight percent or more.

2. The latex polymer of claim 1, wherein the fatty acid of the modified fatty amide (meth)acrylate monomer is derived from linseed oil, soybean oil, coconut oil, safflower oil, or tung oil.

3. The latex polymer of claim 1 wherein the fatty acid of the modified fatty amide (meth)acrylate monomer comprises oleic, linoleic, linolenic, or eleostearic acid.

4. The latex polymer of claim 1 wherein said ethylenically unsaturated monomer is selected from the group consisting of vinyl acetate, vinyl chloride, vinyl ester of a saturated tertiary branched carboxylic acid, acrylonitrile, acrylamide, 2-ethylhexyl acrylate, 2-ethylhexyl methacrylate, 2-hydroxyethyl acrylate, 2-hydroxyethyl methacrylate, glycidyl acrylate, glycidyl methacrylate, acrylic acid, methacrylic acid, butyl acrylate, butyl methacrylate, methyl methacrylate, methyl acrylate, para-acetoxystyrene, and styrene.

5. The latex polymer of claim 1, wherein R' of the fatty amide (meth)acrylate monomer is unsaturated.

6. The latex polymer of claim 1, wherein R' of the fatty amide (meth)acrylate monomer comprises unsaturated straight chain hydrocarbon groups of oleic, linoleic, linolenic or eleostearic fatty acid.

7. The latex polymer of claim 1, wherein R' of the fatty amide (meth)acrylate monomer further comprises saturated straight chain hydrocarbon groups of caprylic, capric, lauric, palmitic, or stearic fatty acid.

8. The latex polymer of claim 1 in which the aqueous dispersed fatty amide (meth)acrylate monomer contains straight chain hydrocarbon groups (R') that are a mixture of unsaturated and saturated straight chain hydrocarbon groups derived from linseed oil, soybean oil, coconut oil, safflower oil or tung oil.

9. A method of forming a latex polymer comprising emulsion polymerizing an aqueous dispersed ethylenically unsaturated monomer suitable for forming a latex composition; and an aqueous dispersed fatty amide (meth)acrylate monomer of the formula:

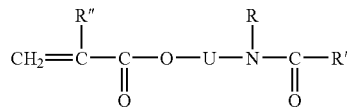

wherein R=CH$_3$, H or CH$_2$CH$_2$OH
    R'=unsaturated or a mixture of unsaturated and saturated straight chain hydrocarbon groups of a fatty acid of a vegetable oil;
    R"=CH$_3$ or H; and
    U =

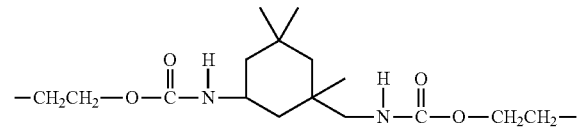

thereby producing a latex polymer and
    wherein the fatty amide (meth)acrylate monomer diffuses through the aqueous phase of the emulsion polymerization and is completely polymerized, and does not separate from the latex, thereby ensuring long-term stability of the latex polymer, and wherein the fatty amide (meth)acrylate monomer content of the latex composition is 18 weight percent or more.

10. The method of claim 9 wherein the fatty acid of the modified fatty amide (meth)acrylate monomer is derived from linseed oil, soybean oil, coconut oil, safflower oil or tung oil.

11. The method of claim 9 wherein the fatty acid of the modified fatty amide (meth)acrylate monomer is oleic, linoleic, linolenic, or eleostearic acid.

12. The method of claim 9 wherein the ethylenically unsaturated monomer is vinyl acetate, vinyl chloride, vinyl ester of a saturated tertiary branched carboxylic acid, acrylonitrile, acrylamide, 2-ethylhexyl acrylate, 2-ethylhexyl methacrylate, 2-hydroxyethyl acrylate, 2-hydroxyethyl methacrylate, glycidyl acrylate, glycidyl methacrylate, acrylic acid, methacrylic acid, butyl acrylate, butyl methacrylate, methyl methacrylate, methyl acrylate, para-acetoxystyrene, or styrene.

13. The method of claim 9 wherein the R' of the fatty amide (meth)acrylate monomer is unsaturated.

14. The method of claim 9 wherein the R' of the fatty amide (meth)acrylate monomer is an unsaturated straight chain hydrocarbon group of oleic, linoleic, linolenic or eleostearic fatty acid.

15. The method of claim 9 wherein the R' of the fatty amide (meth)acrylate monomer further comprises saturated straight chain hydrocarbon groups of caprylic, capric, lauric, palmitic, or stearic fatty acid.

16. The method of forming a latex polymer of claim 9 in which the aqueous dispersed fatty amide (meth)acrylate monomer contains straight chain hydrocarbon groups (R') that are a mixture of unsaturated and saturated straight chain hydrocarbon groups derived from linseed oil, soybean oil, coconut oil, safflower oil or tung oil.

* * * * *

UNITED STATES PATENT AND TRADEMARK OFFICE
CERTIFICATE OF CORRECTION

PATENT NO. : 8,450,414 B2
APPLICATION NO. : 12/331115
DATED : May 28, 2013
INVENTOR(S) : Thames et al.

Page 1 of 1

It is certified that error appears in the above-identified patent and that said Letters Patent is hereby corrected as shown below:

In The Specification

Column 1, line 4 please add the following paragraph to the patent certificate:

STATEMENT OF GOVERNMENT SUPPORT

This invention was made with government support under Agreement No. 2001-38202-10424 with the U.S. Department of Agriculture (USDA) and Award No. N00014-04-1-0703 awarded by the Office of Naval Research (ONR).
The government has certain rights in the invention.

Signed and Sealed this
Second Day of August, 2016

Michelle K. Lee
*Director of the United States Patent and Trademark Office*